(12) United States Patent
Gray (10) Patent No.: US 8,095,123 B2
(45) Date of Patent: Jan. 10, 2012

(54) WIRELESS COMMUNICATION SYSTEM

(75) Inventor: Steven Gray, Charlotte, NC (US)

(73) Assignee: Roche Diagnostics International AG (CH)

( * ) Notice: Subject to any disclaimer, the term of this patent is extended or adjusted under 35 U.S.C. 154(b) by 7 days.

(21) Appl. No.: 11/151,323

(22) Filed: Jun. 13, 2005

(65) Prior Publication Data

US 2006/0281454 A1 Dec. 14, 2006

(51) Int. Cl.
*H04M 3/00* (2006.01)
(52) U.S. Cl. ......... 455/418; 455/419; 455/420; 600/339
(58) Field of Classification Search ............... 340/5.53, 340/539.1, 539.11, 539.12, 539.13, 572.7, 340/573.1, 539.36; 455/420; 600/300, 339, 600/468, 366, 587
See application file for complete search history.

(56) References Cited

U.S. PATENT DOCUMENTS

| 7,138,902 | B2 * | 11/2006 | Menard | 340/5.53 |
|---|---|---|---|---|
| 7,384,403 | B2 * | 6/2008 | Sherman | 600/587 |
| 2003/0040806 | A1 | 2/2003 | MacDonald | |
| 2003/0114836 | A1 | 6/2003 | Estes et al. | |
| 2003/0130708 | A1 * | 7/2003 | Von Arx et al. | 607/60 |
| 2004/0117204 | A1 | 6/2004 | Mazar et al. | |
| 2004/0167464 | A1 | 8/2004 | Ireland et al. | |
| 2005/0033148 | A1 * | 2/2005 | Haueter et al. | 600/407 |
| 2005/0076909 | A1 * | 4/2005 | Stahmann et al. | 128/204.23 |
| 2005/0090993 | A1 * | 4/2005 | Sunshine | 702/21 |
| 2005/0137626 | A1 * | 6/2005 | Pastore et al. | 607/3 |
| 2005/0277872 | A1 * | 12/2005 | Colby et al. | 604/67 |
| 2006/0009817 | A1 * | 1/2006 | Tulkki | 607/60 |
| 2006/0015146 | A1 * | 1/2006 | Girouard et al. | 607/3 |
| 2007/0060869 | A1 | 3/2007 | Tolle et al. | |
| 2007/0060870 | A1 | 3/2007 | Tolle et al. | |
| 2007/0214003 | A1 * | 9/2007 | Holland et al. | 705/2 |
| 2008/0103553 | A1 * | 5/2008 | Penner et al. | 607/60 |

FOREIGN PATENT DOCUMENTS

| EP | 1759726 A2 | 3/2007 |
|---|---|---|
| WO | WO02087681 A2 | 11/2002 |
| WO | WO03009208 A1 | 1/2003 |

OTHER PUBLICATIONS

"RFID External EEPROM Interface IC", ATMEL Corporation, Rev. 1943F-RFID, Apr. 2002, 17 pages.
PCT International Search Report dated Jan. 30, 2007 for PCT/EP2006/005518.

* cited by examiner

*Primary Examiner* — Wayne Cai
*Assistant Examiner* — Julio Perez
(74) *Attorney, Agent, or Firm* — Barnes & Thornburg LLP (57) ABSTRACT

A wireless communication system includes a first device having a communications control circuit configured to initiate transmission of a wireless communication signal, and a second device including a communication interface circuit and a number of other circuits. The communication interface circuit may be responsive to the wireless communication signal to provide information carried by the wireless communication signal to at least one of the other circuits. Alternatively or additionally, the communication interface circuit may be responsive to the wireless communication signal to receive information specified by the wireless communication signal from at least one of the other circuits and to transmit another wireless communication signal carrying the retrieved information back to the first device. In either case, the communication interface circuit is unresponsive to control thereof by any of the number of other circuits. The communications control circuit controls all wireless communication between the first and second devices.

13 Claims, 5 Drawing Sheets

WIRELESS COMMUNICATION SYSTEM

FIELD OF THE INVENTION

The present invention relates generally to the field of wireless communications, and more specifically to systems for conducting wireless communications between a number of devices.

BACKGROUND

Wireless communication between two or more devices may generally be conducted using any of a number of known wireless communication devices and protocols. In some applications, it may be desirable for one of the devices to control all such wireless communications. Examples of such applications include, but are not limited to, wireless communications between at least one ambulatory medical device in the form of an implantable, transcutaneous or transdermal medical device and at least one remote communication device.

SUMMARY

The present invention may comprise one or more of the features recited in the attached claims, and/or one or more of the following features and combinations thereof. A wireless communication system may comprise a first device having a communications control circuit configured to initiate transmission of a wireless communication signal, and a second device having a communication interface circuit coupled to a data interface circuit. The communication interface circuit may be responsive to the wireless communication signal to provide information carried by the wireless communication signal to, or receive information specified by the wireless communication signal from, the data interface circuit. The communications control circuit may control all wireless communication between the first and second devices via control of the wireless communication signal.

The communication interface circuit may be responsive to the wireless communication signal to convert at least a portion of the wireless communication signal to a command signal, wherein the command signal corresponds to one of a command to provide the information carried by the wireless communication signal to the data interface circuit and a command to receive the information from the data interface circuit. If the command signal corresponds to a command to receive information from the data interface circuit, the communication interface circuit may be configured to receive the information from the data interface circuit and transmit the received information back to the first device. The first device may include a wireless communication circuit coupled to the communication control circuit, and the communication control circuit may control all wireless communication between the first and second devices via control of the wireless communication signal. The wireless communication circuit may include a first wireless interface and the communication interface circuit may include a second wireless interface. The wireless communication between the first and second devices may occur via a wireless communication path established between the first and second wireless interfaces. The first wireless interface may include a first inductive interface and the second wireless interface may include a second inductive interface configured to inductively couple to the first inductive interface. The wireless communication path may be established via the inductively coupled first and second inductive interfaces. Alternatively, the first wireless interface may include a first radio frequency (RF) antenna and the second inductive interface may include a second RF antenna. In this case, the wireless communication path may be an RF communication path. Alternatively, the first wireless interface may include a first infrared (IR) interface and the second wireless interface may include a second IR interface. In this case, the wireless communication path may be an IR communication path. Alternatively, the first wireless interface may include a first acoustic interface and the second wireless interface may include a second acoustic interface. In this case, the wireless communication path may be an acoustic communication path. Alternatively, the first wireless interface may include a first conductive interface configured to be coupled to a biological body and the second wireless interface may include a second conductive interface configured to be coupled to the biological body. In this case, the wireless communication path may be the biological body between the first and second conductive interfaces. The first conductive interface may be, for example, a first capacitive interface and the second conductive interface may be, for example, a second capacitive interface. Alternatively, the first wireless interface may include a first optical interface and the second wireless interface may include a second optical interface. In this case, the wireless communication path may be an optical communication path.

The data interface circuit may be a memory circuit. Alternatively, the data interface circuit may be a data processing circuit.

The first device may be an ambulatory medical device for providing a treatment to a body of a patient or monitoring a state of the body, and the second device is a remote communication device. The ambulatory medical device may be implantable into the body of the patient. Alternatively, the ambulatory medical device may be external to the body of the patient. At least a portion of the external ambulatory medical device may extend into the body of the patient, and the external ambulatory medical device may thus be a transcutaneous ambulatory medical device. Alternatively, the external ambulatory medical device may be configured to provide the treatment through the patient's skin, and the external ambulatory medical device may thus be a transdermal ambulatory medical device. The second device may include a plurality of remote communication devices.

Alternatively, the first device may be a communication device and the second device may be an ambulatory medical device for providing a treatment to a body of a patient or monitoring a state of the body. The ambulatory medical device may be implantable into the body of the patient. Alternatively, the ambulatory medical device may be external to the body of the patient. At least a portion of the external ambulatory medical device may extend into the body of the patient, and the external ambulatory medical device may thus be a transcutaneous ambulatory medical device. Alternatively, the external ambulatory medical device may be configured to provide the treatment through the patient's skin, and the external ambulatory medical device may thus be a transdermal ambulatory medical device. The second device may include a plurality of ambulatory medical devices each configured to provide a selected treatment to the body of the patient or to monitor a selected state of the body.

A wireless communication system may comprise a first device having a communications control circuit configured to initiate transmission of a wireless communication signal, and a second device including a communication interface circuit and a number of other circuits. The communication interface circuit may be responsive to the wireless communication signal to provide information carried by the wireless communication signal to at least one of the number of other circuits. Alternatively or additionally, the communication interface circuit may be responsive to the wireless communication signal to receive information specified by the first wireless communication signal from at least one of the number of other circuits and to transmit a second wireless communication signal carrying the retrieved information back to the first device. In either case, the communication interface circuit may be unresponsive to control thereof by any of the number of other circuits.

The first device may include a wireless communication circuit coupled to the communication control circuit. The communication control circuit may control all wireless communication between the first and second devices via control of the wireless communication circuit.

The at least one of the number of other circuits may include a memory circuit. Alternatively, the at least one of the number of other circuits may include a data processing circuit.

The first device may be an ambulatory medical device for providing a treatment to a body of a patient or monitoring a state of the body, and the second device is a remote communication device. The ambulatory medical device may be implantable into the body of the patient. Alternatively, the ambulatory medical device may be external to the body of the patient. At least a portion of the external ambulatory medical device may extend into the body of the patient, and the external ambulatory medical device may thus be a transcutaneous ambulatory medical device. Alternatively, the external ambulatory medical device may be configured to provide the treatment through the patient's skin, and the external ambulatory medical device may thus be a transdermal ambulatory medical device. The second device may include a plurality of remote communication devices.

Alternatively, the first device may be a communication device and the second device may be an ambulatory medical device for providing a treatment to a body of a patient or monitoring a state of the body. The ambulatory medical device may be implantable into the body of the patient. Alternatively, the ambulatory medical device may be external to the body of the patient. At least a portion of the external ambulatory medical device may extend into the body of the patient, and the external ambulatory medical device may thus be a transcutaneous ambulatory medical device. Alternatively, the external ambulatory medical device may be configured to provide the treatment through the patient's skin, and the external ambulatory medical device may thus be a transdermal ambulatory medical device. The second device may include a plurality of ambulatory medical devices each configured to provide a selected treatment to the body of the patient or to monitor a selected state of the body.

DESCRIPTION OF THE ILLUSTRATIVE EMBODIMENTS

For the purposes of promoting an understanding of the principles of the invention, reference will now be made to a number of illustrative embodiments shown in the attached drawings and specific language will be used to describe the same.

Figure 1:
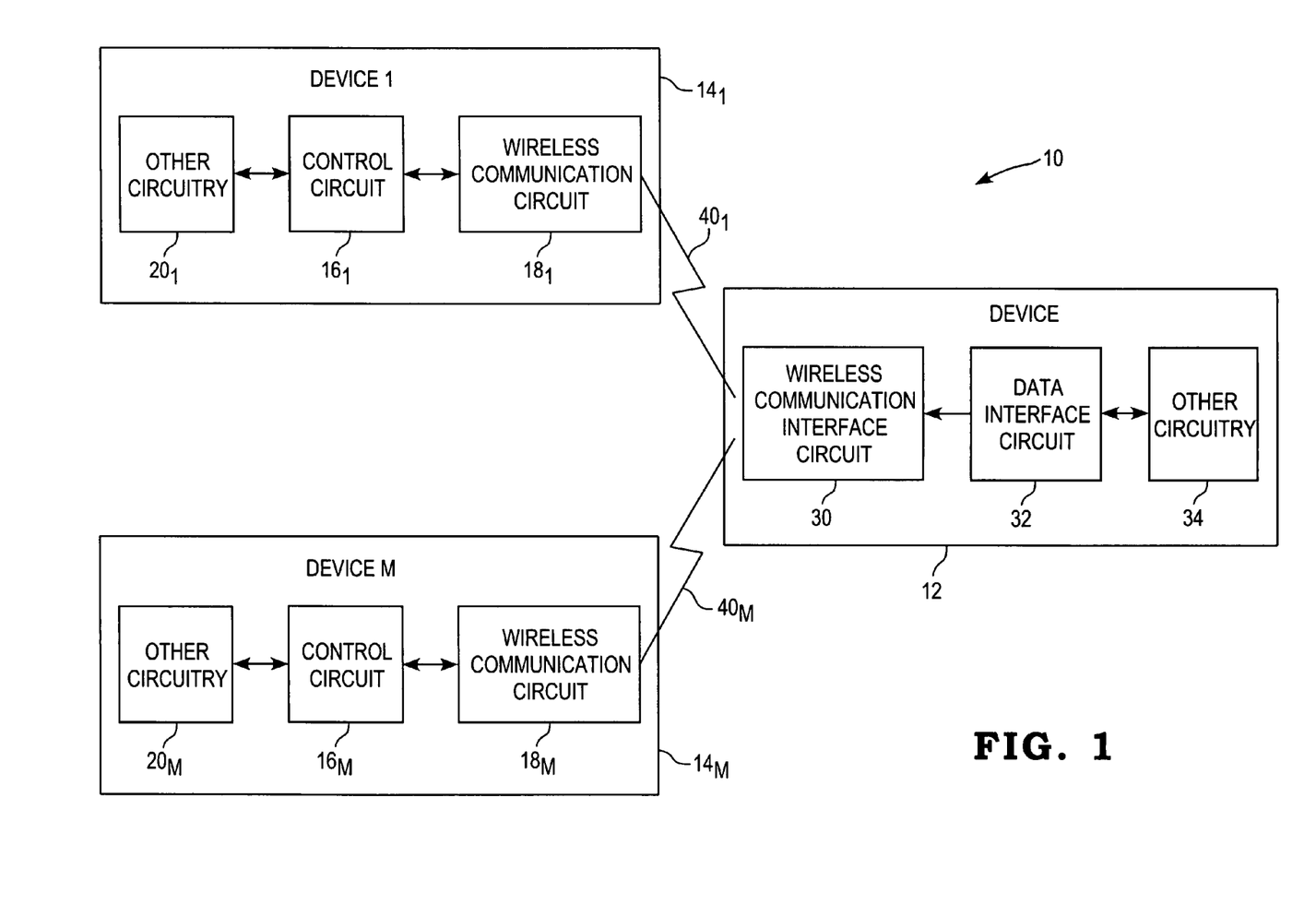
FIG. 1 is a diagram of one embodiment of a wireless communication system.

Referring now to FIG. 1, a block diagram of one illustrative embodiment of a wireless communication system 10 is shown. In the illustrated embodiment, the system 10 includes an electronic device 12 and a separate number, M, of electronic devices $14_1$-$14_M$, of wherein M may be any positive integer.

The electronic device $14_1$ includes at least one control circuit $16_1$ coupled to a wireless communication circuit $18_1$ and also to other circuitry $20_1$ attached to, carried by, or forming part of the electronic device $14_1$. In one embodiment, the control circuit $16_1$ includes one or more conventional processor circuits, and is configured to execute one or more software algorithms for controlling all wireless communications with the electronic device 12 via appropriate control of the wireless communication circuit $18_1$, and for controlling one or more electronic circuits, modules or devices included comprising the other circuitry $20_1$. Alternatively, the control circuit $16_1$ may be or include one or more general-purpose or application-specific processor circuits operable as described hereinafter.

The wireless communication circuit $18_1$ may be or include one or more electronic circuits, modules or devices configured to establish and conduct wireless communications with the electronic device 12. In one embodiment, for example, the electronic device $14_1$ may be configured to only send wireless information to the electronic device 12, and in this embodiment the wireless communication circuit $18_1$ may be or include a conventional transmitter circuit configured to transmit wireless information to the electronic device 12. In an alternative embodiment, the electronic device $14_1$ may be configured to conduct two-way communications with the electronic device. In this embodiment, the electronic device $14_1$ may be configured to transmit and receive wireless information carried by the communication signals to and from the electronic device 12, or may alternatively be configured to only receive wireless information from the electronic device 12. In both such cases, since the control circuit $16_1$ is configured to control all wireless communication with the electronic device 12, the wireless communication circuit $18_1$ will include a conventional transceiver circuit configured to conduct wireless communications with the electronic device 12. In any case, the form of wireless communication used may include, but should not be limited to, radio frequency (RF) communication, infrared (IR) communication, RFID (inductive coupling) communication, acoustic communication, capacitive signaling (through a conductive body), galvanic signaling (through a conductive body), optical communication or the like. In any such case, the wireless communication circuit $18_1$ may further include, as appropriate, one or more antennas, coupling devices, sensors, or the like that may be helpful or necessary to implement or facilitate the chosen form of wireless communication.

The other circuitry $20_1$ may be or include, but should not be limited to, one or more displays, actuators, data input devices, sensors, or the like. The electronic device $14_1$ may be provided in any of a variety of forms including, but not limited to, for example, an implantable device, a transcutaneous or transdermal device configured to be worn by or attached to a user, a compact device configured to be attached to or worn by a user or carried by or within clothing worn by the user, a hand-held device, a notebook or laptop device, a desktop device, or the like. It will be understood that the one or more additional electronic devices $14_M$ include at least the structures and features just described with respect to the electronic device $14_1$.

The electronic device 12 includes a wireless communication interface 30 electrically coupled to a data interface circuit 32 that is electrically coupled to other circuitry 34 attached to, carried by, or forming part of the electronic device 12. In the illustrated embodiment, the wireless communication interface circuit 30 is configured to transfer or receive data only pursuant to commands generated by any one or more of the control circuits $16_1$-$16_M$ and transmitted to the wireless communication interface circuit 30 via the one or more corresponding wireless communication circuits $18_1$-$18_M$. More specifically, the wireless communication interface circuit 30 may only transfer information to the data interface circuit 32 under the control and direction of any one or more of the control circuits $16_1$-$16_M$, and may likewise only transfer data from the data interface circuit 32 to one or more of the electronic devices $14_1$-$14_M$ under the control and direction of the corresponding one or more control circuits $16_1$-$16_M$. No circuitry on-board the electronic device 12, including the data interface 32 or any circuit or device comprising the other circuitry 34, may control wireless communication between the wireless communication interface circuit 30 and any one or more of the electronic devices $14_1$-$14_M$.

Any one or more of the control circuits $16_1$-$16_M$ may establish a corresponding wireless communication link $40_1$-$40_M$, via appropriate control of a corresponding one or more of the wireless communication circuits $18_1$-$18_M$, between a corresponding one of the electronic devices $14_1$-$14_M$ and the electronic device 12. All wireless communications between any one or more of the electronic devices $14_1$-$14_M$ are conducted via a corresponding one or more of the wireless communication links $40_1$-$40_M$, under the complete control of the corresponding one or more of the control circuits $16_1$-$16_M$. In embodiments of the system 10 wherein any one or more of the communication links $40_1$-$40_M$ between the electronic device 12 and any one or more corresponding electronic devices $14_1$-$14_M$ are inductive links, the corresponding one or more communication circuits $16_1$-$16_M$ need not control the corresponding one or more wireless communication circuits $18_1$-$18_M$ to initiate operation of the wireless communication interface circuit 30. Rather, operation of the wireless communication interface circuit 30 in such embodiments, to transmit or receive data, may be initiated in response to establishment of the inductive coupling between the wireless communication interface circuit 30 and one or more of the wireless communication circuits $18_1$-$18_M$. In some embodiments, for example, as will be described in greater detail hereinafter, the wireless communication interface circuit 30 may derive its operating power from such an inductive coupling, and in such cases the wireless communication interface circuit 30 may be responsive to power up to initiate transmission or reception of data. Thereafter, all communication between the electronic device 12 and any one or more of the electronic devices $14_1$-$14_M$ will be controlled by the corresponding one or more wireless communication circuits $16_1$-$16_M$.

It will be understood that the electronic device 12 and any of the devices $14_1$-$14_M$ may alternatively or additionally include multiple wireless communication interfaces to allow any such device 12 and/or $14_1$-$14_M$ to communicate with one or more other devices according to any number of different wireless communication techniques or protocols. This may be accomplished by providing multiple telemetry interfaces for the wireless communication interface circuit 30 and/or any of the wireless communication circuits $18_1$-$18_M$, or by providing multiple wireless communication interface circuits 30 and/or wireless communication circuits $18_1$-$18_M$ in any one corresponding device 12 and/or $14_1$-$14_M$ with each such wireless communication interface circuit 30 and/or wireless communication circuit $18_1$-$18_M$ having a different dedicated telemetry interface.

In the illustrated embodiment, the data interface circuit 32 is configured to receive information provided thereto by the wireless communication interface circuit 30, generally under control of one or more of the control circuits $16_1$-$16_M$ of the one or more corresponding electronic devices $14_1$-$14_M$, and/or to provide information to the wireless communication interface circuit 30 generally at the request of one or more of the control circuits $16_1$-$16_M$. In the later case, the wireless communication interface circuit 30 is responsive to commands generated by one or more of the control circuits $16_1$-$16_M$ and received wirelessly via a corresponding one or more of the wireless communication links $40_1$-$40_M$, to retrieve information specified by such commands from the data interface circuit 32, and to transmit or transfer the requested information back to the one or more control circuits $16_1$-$16_M$ via an appropriate one or more of the communication links $40_1$-$40_M$.

In one embodiment, the data interface circuit 32 includes at least one processor circuit configured to comply with and act upon commands produced by the one or more control circuits $16_1$-$16_M$ and provided thereto via the wireless communication interface circuit 30. In this embodiment, the one or more processor circuits may further be configured to control one or more circuits or other electrical components included within the other circuitry 34. In an alternative embodiment, the data interface circuit 30 may instead be or include one or more state machines configured to comply with and act upon commands produced by one or more of the control circuits $16_1$-$16_M$ and provided thereto via the wireless communication interface circuit 30. In this embodiment, the other circuitry 34 may or may not include one or more processor circuits. In yet another embodiment, the data interface circuit 32 may be or include at least one memory device responsive to commands, produced by one or more of the control circuits $16_1$-$16_M$ and transmitted wirelessly to the wireless communication circuit 30, to store data provided thereto by the wireless communication interface circuit 30 in one or more specified memory locations, and/or to provide data located in one or more specified memory locations to the wireless communication interface circuit 30 for transfer back to the one or more control circuits $16_1$-$16_M$ via a corresponding one or more of the communication links $40_1$-$40_M$. In this embodiment, the other circuitry 34 may include one or more processor circuits or one or more state machines, configured to provide data to and receive data from the one or more memory devices comprising the data interface circuit 32.

Generally, the other circuitry 34 may be or include, but should not be limited to, one or more displays, actuators, data input devices, sensors, or the like. The electronic device 12 may be provided in any of a variety of forms including, but not limited to, for example, an implantable device, a transcutaneous or transdermal device configured to be worn by or attached to a user, a compact device configured to be carried by or within clothing worn by the user, a hand-held device, a notebook or laptop device, a desktop device, or the like.

The control circuits $16_1$-$16_M$ are each configured to produce a number of different types of commands. One type of command is configured to direct the wireless communication interface circuit 30 to provide information carried by this type of command to the data interface circuit 32. Another type of command is configured to direct the wireless communication interface circuit 30 to retrieve information specified by this type of command from the data interface circuit 32 and to wirelessly transmit the retrieved information. Yet another type of command is configured to direct the wireless communication interface circuit 30 to poll the data interface circuit 32 for information and to wirelessly transmit any polled information. The polled information may illustratively correspond to new information existing in the device 12 since generation of a previous one of this type of command. Generally, this type of command may illustratively be configured to direct the wireless communication interface circuit 30 to wirelessly transmit the new information only when the new information is available in the device 12. In any case, any of the foregoing types of commands are carried by wireless communication signals transmitted to the device 12.

The wireless communication interface circuit 30 is generally responsive to the wireless communication signals received from any one or more of the electronic devices $14_1$-$14_M$ to convert at least a portion of the wireless communication signals back to corresponding ones of the various command signals. The wireless communication interface circuit 30 is then responsive to one type of command to provide information to the data interface circuit 32, to the another type of command to retrieve information from the data interface circuit 32 and wirelessly transmit the retrieved information, and to yet another type of command to poll the data interface circuit 32 for information as described hereinabove, and to wirelessly transmit any polled information.

Figure 2:
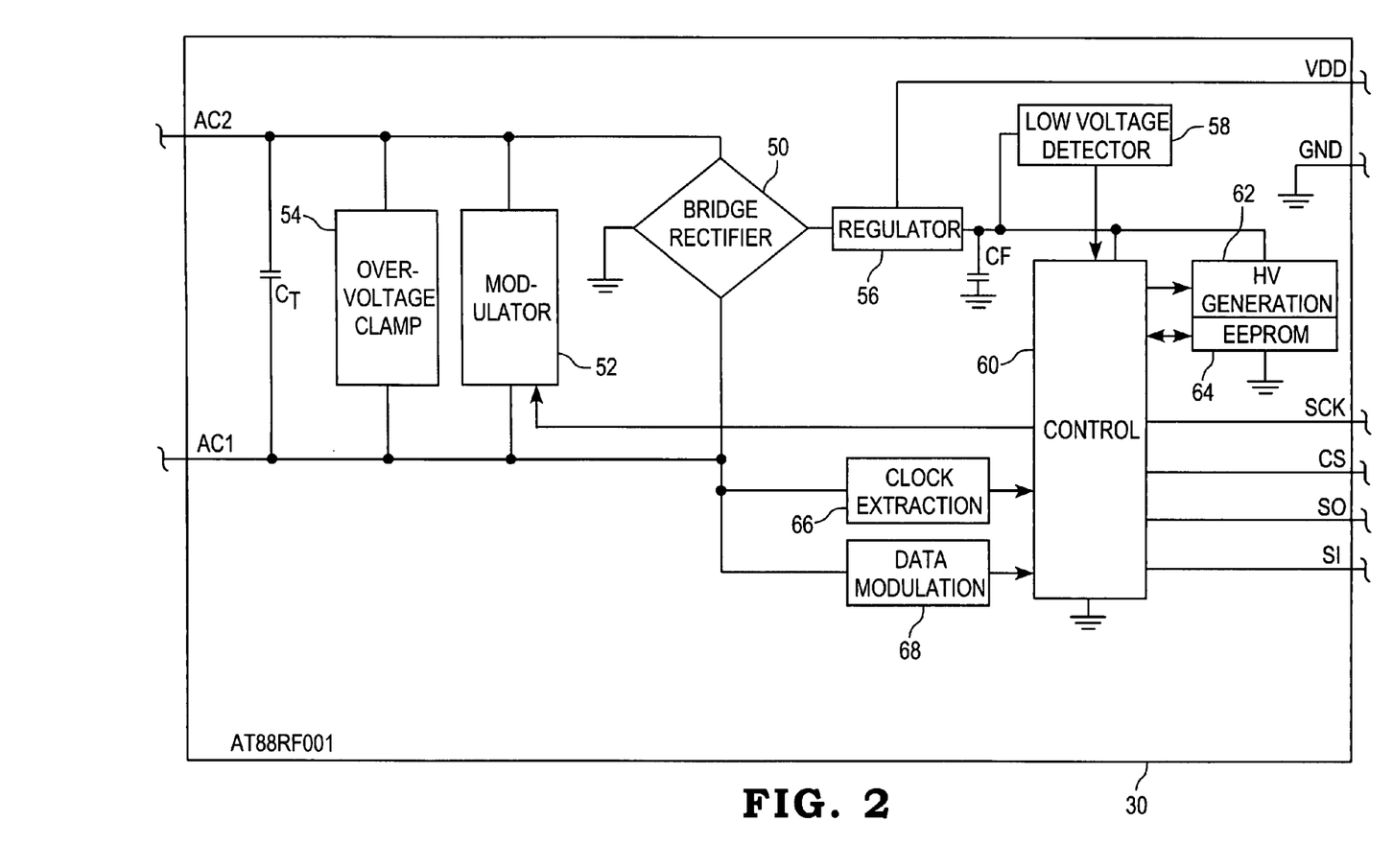
FIG. 2 is a schematic diagram of one embodiment of the wireless communication interface circuit shown in FIG. 1.

Referring now to FIG. 2, a block diagram of one illustrative embodiment of the wireless communication interface circuit 30 of FIG. 1 is shown. In the illustrated embodiment, the wireless communication interface circuit 30 includes a bridge rectifier circuit 50 having a first circuit input electrically connected to a first communication signal input, AC1, and a second input electrically connected to a second communication signal input AC2. Also electrically connected between the communication signal inputs AC1 and AC2 are a modulator circuit 52, an over-voltage clamp circuit 54 and a trim capacitor $C_T$. An output of the bridge rectifier 50 is electrically connected to a voltage regulator 56. The bridge rectifier circuit 50 is responsive to the energy present in the wireless communication link ($40_1$-$40_M$) to produce a DC voltage which is supplied to the voltage regulator 56. The voltage regulator 56 is responsive to this DC voltage to produce a supply voltage, VDD, which is used to power all internal circuitry of the wireless communication interface circuit 30, and which may further be used as the supply voltage to one or more circuits external to the wireless communication interface circuit 30. The supply voltage produced by the regulator circuit 56 is provided to a low voltage detector circuit 58, to a control circuit 60 and also to a high-voltage generation circuit 62. An EEPROM 64 is also electrically connected to the control circuit 60. A clock extraction circuit 66 is electrically coupled between the communication signal input AC1 and the control circuit 60, and a data modulation circuit 68 is likewise electrically coupled between the communication signal input, AC1, and the control circuit 60. An output of the control circuit 60 is connected to the modulator circuit 52.

As just described, the bridge rectifier circuit 50 is responsive to the communication signal supplied to the communication signal inputs AC1 and AC2 to supply a DC voltage to the voltage regulator circuit 56 which, in turn, provides a supply voltage, VDD, to all internal circuitry. The illustrated wireless communication interface circuit 30 is thus self-powered by extracting its supply voltage from the communication signal establishing the communication link $40_1$-$40_M$. The clock extraction circuit 66 and data modulation circuit 68 extract timing and data information from the communication signals provided to the communication signal inputs, AC1 and AC2, and provide this information to the control circuit 60. From this information, the control circuit 60 generates a clock signal, SCK, a chip select signal, CS, and a data output signal, SO. Information is transferred from the wireless communication circuit 30 to the data interface circuit 32 using the SCK, CS and SO outputs of the control circuit 60. Incoming data provided by the data interface circuit 32 enters the control circuit 60 via a data input signal path, SI, and the control circuit 60 may provide any such data back to any one or more of the electronic devices $14_1$-$14_M$ by appropriately controlling the modulator circuit 52 to send corresponding wireless communication signals back to the one or more electronic devices $14_1$-$14_M$ via the communication signal ports AC1 and AC2.

The block diagram of the wireless communication interface circuit 30 illustrated in FIG. 2 is representative of an RFID external EEPROM interface circuit number AT88RF001 that is commercially available from Atmel Corporation of San Jose, Calif. The AT88RF001 is a stand-alone 13.56 MHz, RFID front end circuit that includes a serial port suitable for connection to an external high-density serial memory or other electronic devices. Using the on-board EEPROM 64, the AT88RF001 can be configured to communicate using various protocols, and can interface to both two-wire and SPI external devices. The AT88RF001 contains 320 bits of full read/write EEPROM memory 64, and offers features such as passwords, locking and a variable-length ID. It is electrically compatible with ISO/IEC 14443-2, type B technology. The AT88RF001 circuit includes an internal tuning capacitor, $C_T$, thereby requiring only an external coil antenna to complete the RFID channel. The serial port is configurable to communicate with external circuits using either two-wire or four-wire (SPI) serial channels, at a maximum speed of 106 kilobits per second (Kbps). It will be noted that in other embodiments of the wireless communication circuit 30, other conventional interfaces may be used. Further details relating to the structure and operation of the AT88RF001 circuit may be found in Atmel® Publication No. 1943F-RFID-04/02, ©2002 Atmel Corporation, the contents of which are incorporated herein by reference.

A number of specific example implementations of the wireless communication system 10 of FIG. 1 will now be provided. In the first two following examples, the wireless communication interface circuit 30 will be described as being implemented with the AT88RF001 circuit illustrated and described with respect to FIG. 2, although it will be understood that the wireless communication interface circuit 30 may alternatively be provided in the form of one or more general-purpose or application specific circuits operable as described with respect to FIG. 1 and as will be described in the examples that follow.

Example 1

Figure 3:
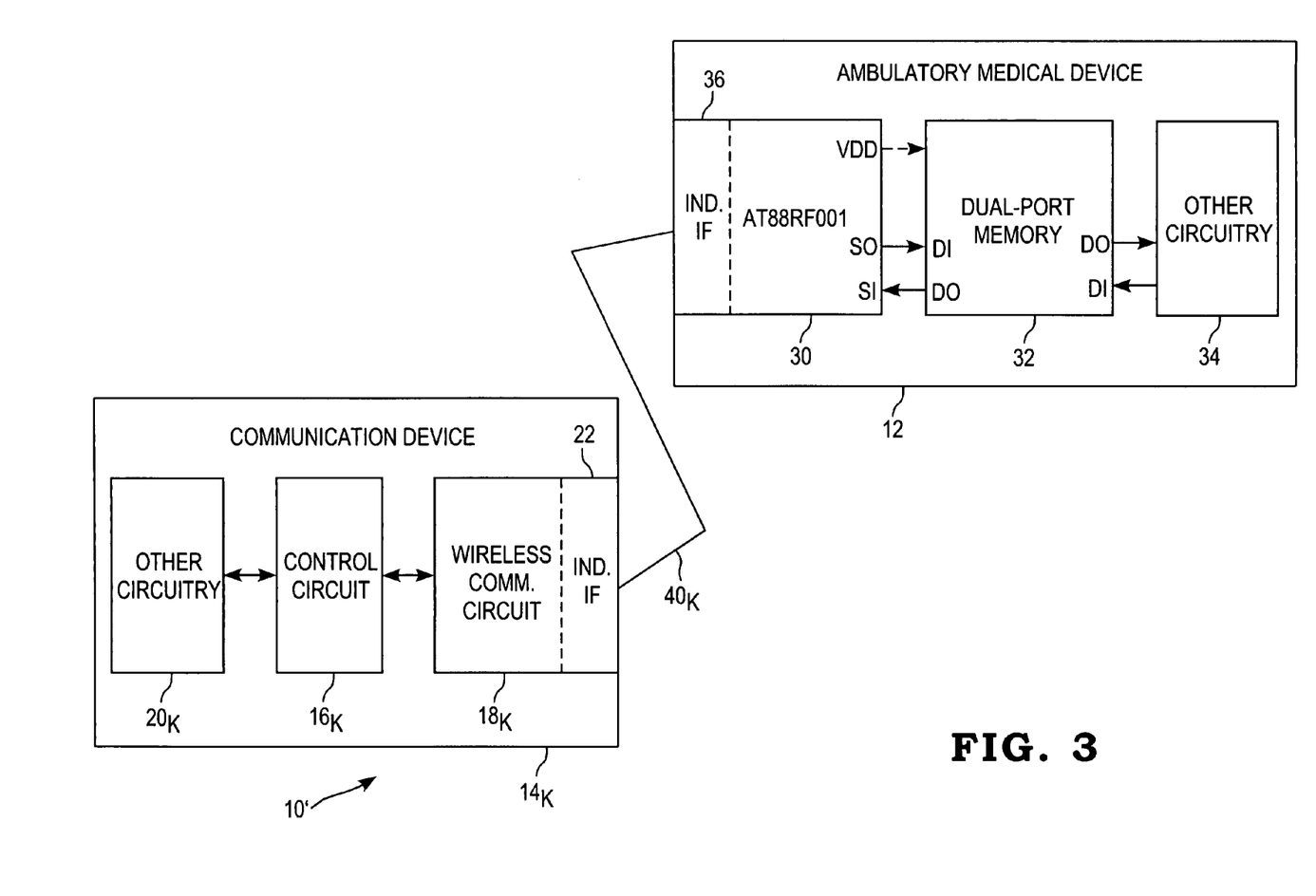
FIG. 3 is a diagram of one embodiment of the wireless communication system of FIG. 1 using the wireless communication interface circuit of FIG. 2.

Referring now to FIG. 3, one specific example implementation 10' of the wireless communication system 10 of FIG. 1 is shown. In this example, any number, M, of electronic devices $14_1$-$14_M$ may be included, although only one such electronic device $14_K$ is shown, and will be described, for ease of explanation. In this example, the electronic device 12 is provided in the form of an ambulatory medical device that may be implanted into a body of a human or an animal, or may alternatively be an external device that interfaces with the body of a human or an animal. In embodiments where the ambulatory medical device is an external device, the medical device may be a transcutaneous device having at least a portion of the device extending into the body of the patient. Alternatively, the external medical device may be a transdermal device configured to provide the treatment through the patient's skin. The ambulatory medical device 12 may be a device or system for monitoring one or more conditions; e.g., an analyte, of the human or animal, or may alternatively be a device or system for controllably providing medical therapy to a human or animal in the form of a drug; e.g., insulin, or other medicine, or other therapeutic treatment. Examples of such an ambulatory medical device 12 may include, but are not limited to, drug infusion devices, cardiac or other monitoring devices, or the like.

In the illustrated embodiment, the electronic device $14_K$ is a communication device separate from the ambulatory medical device 12, and which may be provided in the form of a hand-held or other portable device, or in the form of a desktop or other stationary device, as described hereinabove with respect to FIG. 1.

In the illustrated embodiment, the wireless communication circuit $18_K$ includes an inductive interface 22, such as a suitable coil, and another inductive interface 36, such as another suitable coil, is electrically coupled to the communication signal ports AC1 and AC2 of the AT88RF001 wireless communication interface circuit 30. The wireless communication link $40_K$ is thus established via inductively coupling between the inductive interfaces 22 and 36 in a conventional manner that allows wireless communication to be conducted over such an inductive link.

In the illustrated embodiment, the data interface circuit 32 is provided in the form of a conventional dual-port memory device having a first data input port electrically connected to the data output port, SO, of the AT88RF001 wireless communication interface circuit 30, and a first data output port electrically connected to the data input port, SI, of the AT88RF001 wireless communication interface circuit 30. A second data output port is electrically connected to the other circuitry 34, and the second data input port is also electrically connected to the other circuitry 34. The other circuitry 34, in this embodiment, includes a microprocessor or other processor circuit, or alternatively a state machine, configured to receive data from the second data output port of the dual-port memory device 32, and to send data to the second data input port of the dual-port memory device 32. The other circuitry 34 may further include one or more actuators, sensors, display devices, data input devices, and the like, as described hereinabove with respect to FIG. 1. Likewise, the other circuitry $20_K$ of the communication device $14_K$ may include one or more actuators, sensors, display devices, data input devices, or the like.

In one embodiment of the wireless communication system 10' illustrated in FIG. 3, the control circuit $16_K$ of the communication device $14_K$ is configured to only send information to the ambulatory medical device 12, so that only one-way communication occurs from the communication device $14_K$ to the ambulatory medical device 12. In this embodiment, the wireless communication circuit $18_K$ includes a transmitter circuit responsive to commands produced by the control circuit $16_K$ to transmit commands via the wireless communication link $40_K$ to the AT88RF001 wireless communication interface circuit 30 of the ambulatory medical device 12, wherein such commands include instructions to write specified values of data to specified addresses or address blocks in the dual-port memory device 32. In an alternate embodiment, the control circuit $16_K$ of the communication device $14_K$ is configured to only receive information from the ambulatory medical device 12, so that only one-way communication occurs from the ambulatory medical device 12 to the communication device $14_K$. In this embodiment, the wireless communication circuit $18_K$ includes a transceiver circuit responsive to the control circuit $16_K$ to send commands generated by the control circuit $16_K$ via the wireless communication link $40_K$ to the AT88RF001 wireless communication interface circuit 30, wherein such commands include instructions to retrieve data values from specified addresses or address blocks in the dual-port memory 32, and to transmit the retrieved data values back to the transceiver circuit $18_K$ via the wireless communication link $40_K$. The retrieved data values are then provided by the transceiver circuit $18_K$ back to the control circuit $16_K$. In still another embodiment, the control circuit $16_K$ is operable to control transmission of information to the ambulatory medical device 12 and receipt of specified of information back from the ambulatory medical device 12, to thereby control two-way communication between the communication device $14_K$ and the ambulatory medical device 12. In this embodiment, the control circuit $16_K$, is operable as described previously in this example, to transmit data to, and receive data from, the AT88RF001 wireless communication interface circuit 30. In each of these foregoing embodiments, the dual-port memory circuit 32 carries out the requested operation, and returns its response to the AT88RF001 wireless communication interface circuit 30 according to the selected serial communications protocol. The AT88RF001 wireless communication interface circuit 30 converts all commands and responses to suitable data protocols usable by the various devices and circuits acting upon them.

Independent of the operation of the AT88RF001 wireless communication interface circuit 30, the microprocessor or other processor circuit, or state machine included in the other circuitry 34, uses the second data input and output ports of the dual-port memory circuits 32 to read and write appropriate data values therefrom and thereto. It will be understood, however, that any other such microprocessor, other processor circuit or state machine, cannot initiate or control data communication with the AT88RF001 wireless communication interface circuit 30. Rather, only the control circuit $16_K$ of the communication device $14_K$ can control the AT88RF001 wireless communication interface circuit 30 to transfer data between the ambulatory medical device 12 and the communication device $14_K$.

Example 2

Figure 4:
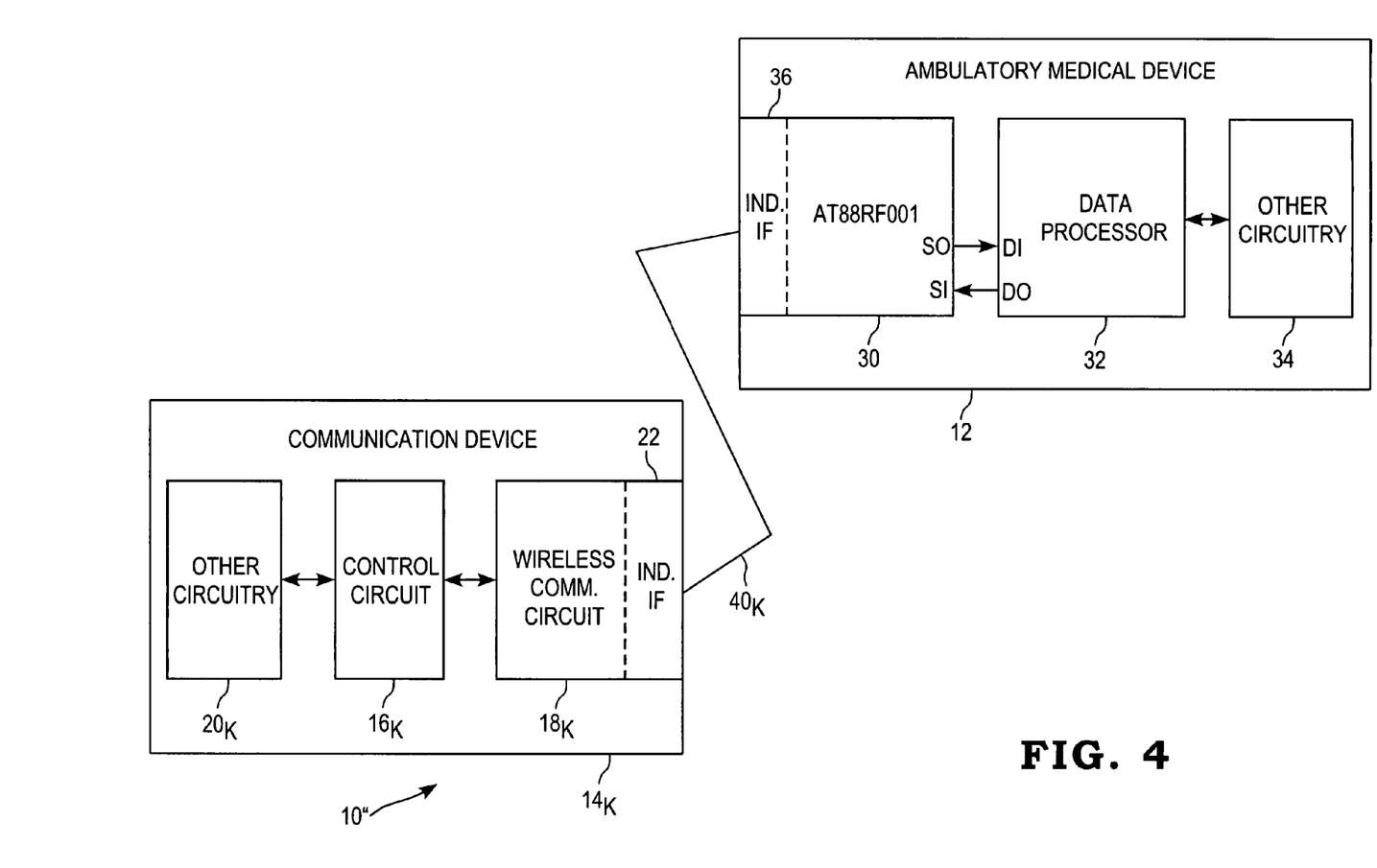
FIG. 4 is a diagram of an alternate embodiment of the wireless communication system of FIG. 1 using the wireless communication interface circuit of FIG. 2.

Referring now to FIG. 4, another specific example implementation 10″ of the wireless communication system 10 of FIG. 1 is shown. In this example, any number, M, of electronic devices $14_1$-$14_M$ may be included, although only one such electronic device $14_K$ is shown, and will be described, for ease of explanation. In this example, the electronic devices 12 and 14 are each identical in many respects to the example implementation illustrated and described with respect to FIG. 3, and like numbers are therefore used to identify like components. However, in the example implementation 10″, the data interface circuit 32 is provided in the form of a data processor, which may be implemented with one or more conventional processor circuits or state machines. In this implementation, the communication device $14_K$ and AT88RF0001 wireless communication circuit 30 behave identically as described in example 1 above, and the data processor 32 is configured to emulate the functions of the memory device described in example 1.

Example 3

Figure 5:
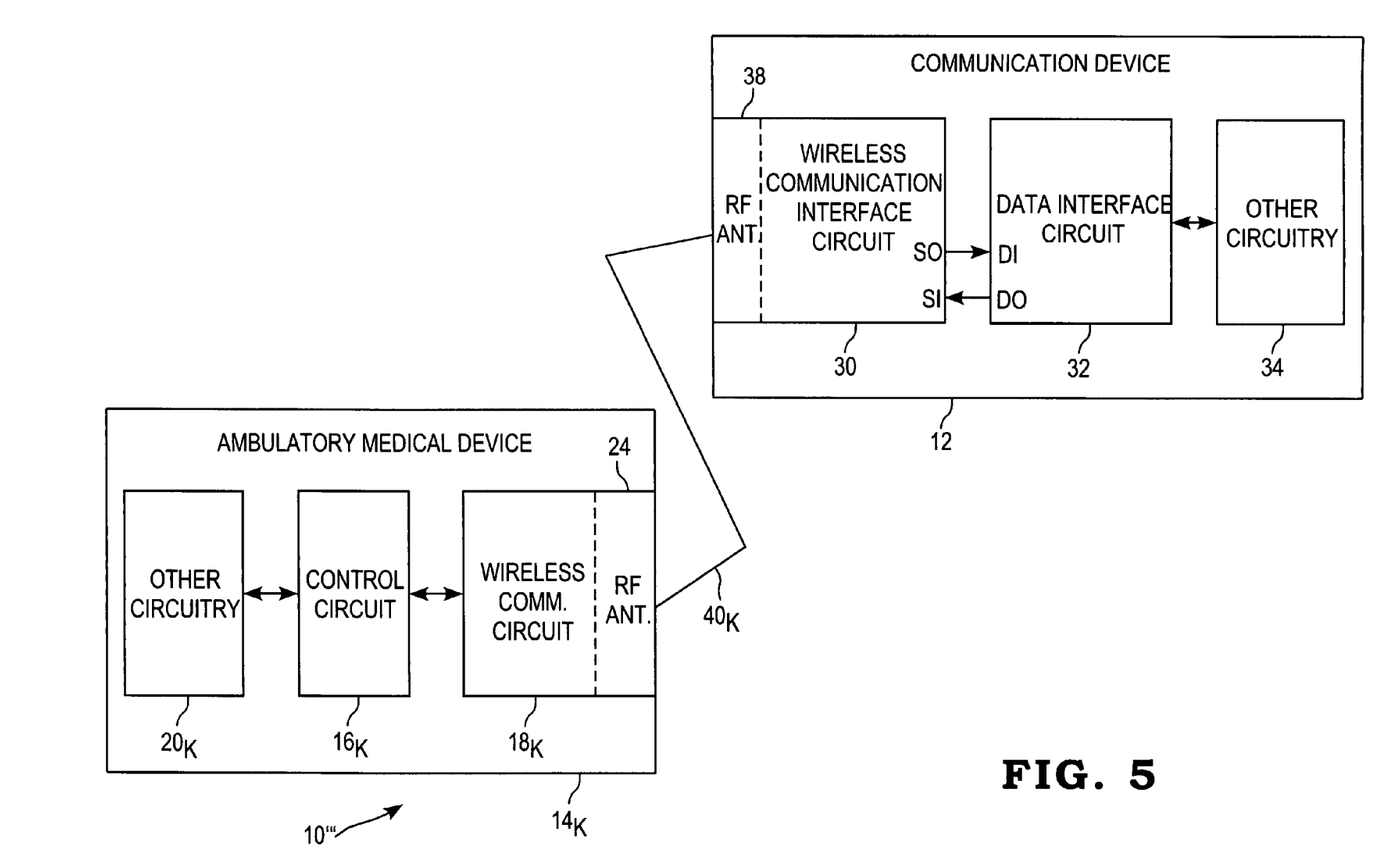
FIG. 5 is a diagram of another alternate embodiment of the wireless communication system of FIG. 1 using the wireless communication interface circuit of FIG. 2.

Referring now to FIG. 5, yet another specific example implementation 10‴ of the wireless communication system 10 of FIG. 1 is shown. In this example, any number, M, of electronic devices $14_1$-$14_M$ may be included, although only one such electronic device $14_K$ is shown, and will be described, for ease of explanation. In this example, the electronic device 12 is provided in the form of a communication device and the electronic device $14_K$ is provided in the form of an ambulatory medical device. The communication device 12 may be provided in the form of a hand-held or other portable device, or in the form of a desktop or other stationary device, as described hereinabove with respect to FIG. 1. The ambulatory medical device $14_K$, on the other hand, may be implanted into a body of a human or an animal, or may alternatively be an external device that interfaces with the body of a human or an animal. In embodiments where the ambulatory medical device is an external device, the medical device may be a transcutaneous device having at least a portion of the device extending into the body of the patient. Alternatively, the external medical device may be a transdermal device configured to provide the treatment through the patient's skin. The ambulatory medical device $14_K$ may be a device or system for monitoring one or more conditions; e.g., an analyte, of the human or animal, or may alternatively be a device or system for controllably providing medical therapy to a human or animal in the form of a drug; e.g., insulin, or other medicine, or other therapeutic treatment. Examples of such an ambulatory medical device $14_K$ may include, but are not limited to, drug infusion devices, cardiac or other monitoring devices, or the like.

In the illustrated embodiment, the wireless communication circuit $18_K$ includes a conventional RF antenna 24, and another conventional RF antenna 38 is electrically coupled to the wireless communication interface circuit 30. The AT88RF001 generally does not support RF communications via the signal ports AC1 and AC2, and one or more other conventional circuits comprise the wireless communication interface circuit 30 in the embodiment illustrated in FIG. 5. The wireless communication interface circuit 30 in the embodiment illustrated in FIG. 5 is otherwise operable as described herein. The wireless communication link $40_K$ is thus established via an RF communication link between the antennas 24 and 38 in a conventional manner that allows wireless communication to be conducted over such an RF link.

In the illustrated embodiment, the data interface circuit 32 may be provided in the form of a conventional dual-port memory device, such as illustrated and described with respect to FIG. 3, or may alternatively be provided in the form of a processor circuit or state machine, such as illustrated and described with respect to FIG. 4.

In one embodiment of the wireless communication system 10''' illustrated in FIG. 5, the control circuit $16_K$ of the ambulatory medical device $14_K$ is configured to only send information to the communication device 12, so that only one-way communication occurs from the ambulatory medical device $14_K$ to the communication device 12. In this embodiment, the wireless communication circuit $18_K$ includes a transmitter circuit responsive to commands produced by the control circuit $16_K$ to transmit commands via the wireless communication link $40_K$ to the wireless communication interface circuit 30 of the communication device 12, wherein such commands include instructions to write specified values of data to the data interface device 32. In an alternate embodiment, the control circuit $16_K$ of the ambulatory medical device $14_K$ is configured to only receive information from the communication device 12, so that only one-way communication occurs from the communication device 12 to the ambulatory medical device $14_K$. In this embodiment, the wireless communication circuit $18_K$ includes a transceiver circuit responsive to the control circuit $16_K$ to send commands generated by the control circuit $16_K$ via the wireless communication link $40_K$ to the wireless communication interface circuit 30, wherein such commands include instructions to retrieve data values from the data interface device 32, and to transmit the retrieved data values back to the transceiver circuit $18_K$ via the wireless communication link $40_K$. The retrieved data values are then provided by the transceiver circuit $18_K$ back to the control circuit $16_K$. In still another embodiment, the control circuit $16_K$ is operable to control transmission of information to the communication device 12 and receipt of specified of information back from the communication device 12, to thereby control two-way communication between the ambulatory medical device $14_K$ and the communication device 12. In this embodiment, the control circuit $16_K$, is operable as described previously in this example, to transmit data to, and receive data from, the wireless communication interface circuit 30. In each of these foregoing embodiments, the data interface circuit 32 carries out the requested operation, and returns its response to the wireless communication interface circuit 30 according to the selected serial communications or other conventional protocol. The wireless communication interface circuit 30 converts all commands and responses to suitable data protocols usable by the various devices and circuits acting upon them.

Those skilled in the art will recognize other example implementations of the wireless communication circuit 10 of FIG. 1, and any other such example implementation is contemplated by this disclosure.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected. For example, in any embodiment described herein, any of the one or more control circuits $16_1$-$16_M$ may "poll" the electronic device 12, in a conventional manner, at specified intervals to thereby periodically request any new information from the electronic device 12.

What is claimed is:

1. A wireless communication system comprising:
   a first electronic device having a first control circuit configured to initiate transmission by the first electronic device of a wireless communication signal, and
   a second electronic device having a communication interface circuit electrically connected to a data interface circuit, the communication interface circuit having a second control circuit and circuitry responsive to energy present in the wireless communication signal to produce a supply voltage used to power the second control circuit, the second control circuit configured to convert at least a portion of the wireless communication signal to a command signal corresponding to one of a first command to provide first information carried by the wireless communication signal to the data interface circuit, a second command to receive second information specified by the wireless communication signal from the data interface circuit and a third command to poll the data interface circuit for third information, the second control circuit configured to be responsive to the first command to provide the first information to the data interface circuit, to the second command to receive the second information from the data interface circuit and control the communication interface circuit to wirelessly transmit the second information and to the third command to poll the data interface circuit for the third information and control the communication interface circuit to wirelessly transmit the third information only if the data interface circuit contains the third information, and wherein no circuitry on-board the second electronic device controls wireless communication between the communication interface circuit of the second electronic device and the first control circuit, and the first control circuit is instead configured to control all wireless communication between the first and second electronic devices via control of the wireless communication signal.

2. The wireless communication system of claim 1 wherein the supply voltage produced by the circuitry responsive to energy present in the wireless communication signal to produce a supply voltage is further used to power the data interface circuit.

3. The wireless communication system of claim 1 wherein the circuitry responsive to energy present in the wireless communication signal to produce a supply voltage comprises:
- a bridge rectifier responsive to the energy present in the wireless communication signal to produce a DC voltage, and
- a voltage regulator responsive to the DC voltage produced by the bridge rectifier to produce the supply voltage.

4. The wireless communication system of claim 1 wherein the data interface circuit is a memory circuit.

5. The wireless communication system of claim 1 wherein the data interface circuit is a data processing circuit.

6. The wireless communication system of claim 1 wherein the first electronic device is an ambulatory medical device configured to provide a treatment to a body of a patient or to monitor a state of the body, and the second electronic device is a remote communication device.

7. The wireless communication system of claim 6 wherein the ambulatory medical device is configured to administer insulin to the body of the patient.

8. The wireless communication system of claim 6 wherein the ambulatory medical device is configured to monitor an analyte of the patient's body.

9. The wireless communication system of claim 6 wherein the second electronic device comprises a plurality of remote communication devices.

10. The wireless communication system of claim 1 wherein the first electronic device is a communication device and the second electronic device is an ambulatory medical device configured to provide a treatment to a body of a patient or to monitor a state of the body.

11. The wireless communication system of claim 10 wherein the ambulatory medical device is configured to administer insulin to the body of the patient.

12. The wireless communication system of claim 10 wherein the ambulatory medical device is configured to monitor an analyte of the patient's body.

13. The wireless communication system of claim 10 wherein the second electronic device comprises a plurality of ambulatory medical devices each configured to provide a selected treatment to the body of the patient or to monitor a selected state of the body.

* * * * *